United States Patent
Stanwich et al.

(10) Patent No.: US 6,482,007 B2
(45) Date of Patent: Nov. 19, 2002

(54) DENTAL WEDGE WITH HANDLE

(75) Inventors: Lawrence J. Stanwich, Boston, MA (US); Anthony R. Silvestri, Jr., Plymouth, MA (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 09/747,596

(22) Filed: Dec. 22, 2000

(65) Prior Publication Data

US 2002/0081552 A1 Jun. 27, 2002

(51) Int. Cl.[7] .................................................. A61C 3/00
(52) U.S. Cl. ....................................................... 433/149
(58) Field of Search ..................... 433/149, 39; 132/329

(56) References Cited

U.S. PATENT DOCUMENTS

| | | | | |
|---|---|---|---|---|
| 3,636,631 A | * | 1/1972 | Tofflemire | 433/149 |
| 3,783,883 A | * | 1/1974 | Alexander | 132/323 |
| 4,696,646 A | * | 9/1987 | Maitland | 433/149 |
| 4,747,777 A | * | 5/1988 | Ward | 433/141 |
| 4,805,646 A | * | 2/1989 | Shimenkov | 132/329 |
| 5,890,901 A | | 4/1999 | Fischer et al. | 433/149 |
| 6,074,210 A | | 6/2000 | Garrison | 433/149 |
| 6,135,771 A | * | 10/2000 | Dragan et al. | 433/90 |

* cited by examiner

*Primary Examiner*—John J. Wilson
*Assistant Examiner*—Melba Bumgarner
(74) *Attorney, Agent, or Firm*—Fattibene & Fattibene; Paul A. Fattibene; Arthur T. Fattibene

(57) ABSTRACT

A dental wedge having a handle portion attached to the dental wedge portion for use in separating teeth. The handle portion facilitates positioning and insertion of the dental wedge portion between teeth. The handle portion may be frangibly attached to the dental wedge portion. In another embodiment, the handle portion may have a bendable portion to facilitate positioning of the dental wedge portion. The dental wedge portion may be of a variety of different shapes. The dental wedge portion and handle portion greatly facilitates positioning of the dental wedge portion between teeth and adjacent a matrix band utilized in a dental restoration.

12 Claims, 3 Drawing Sheets

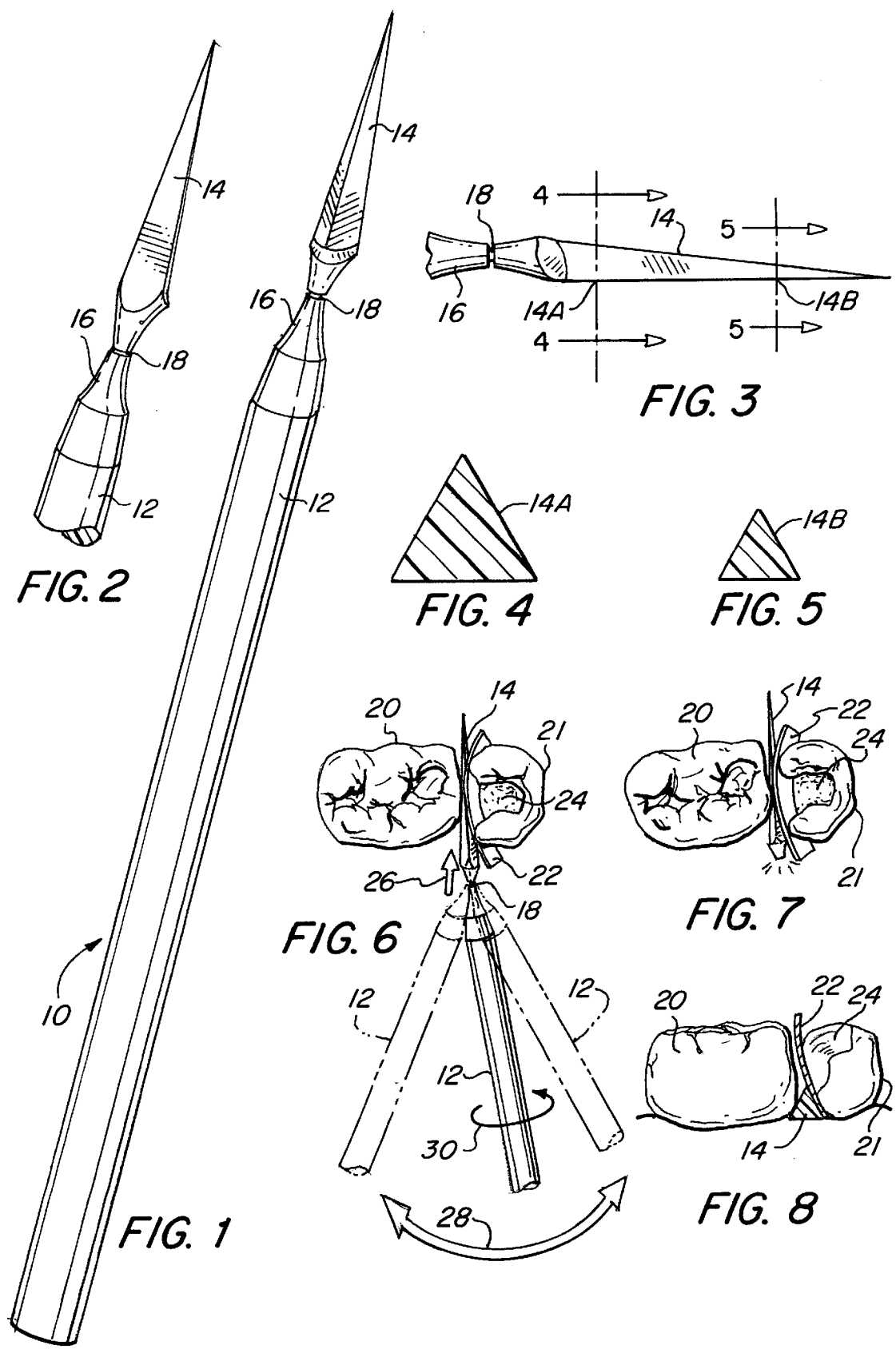

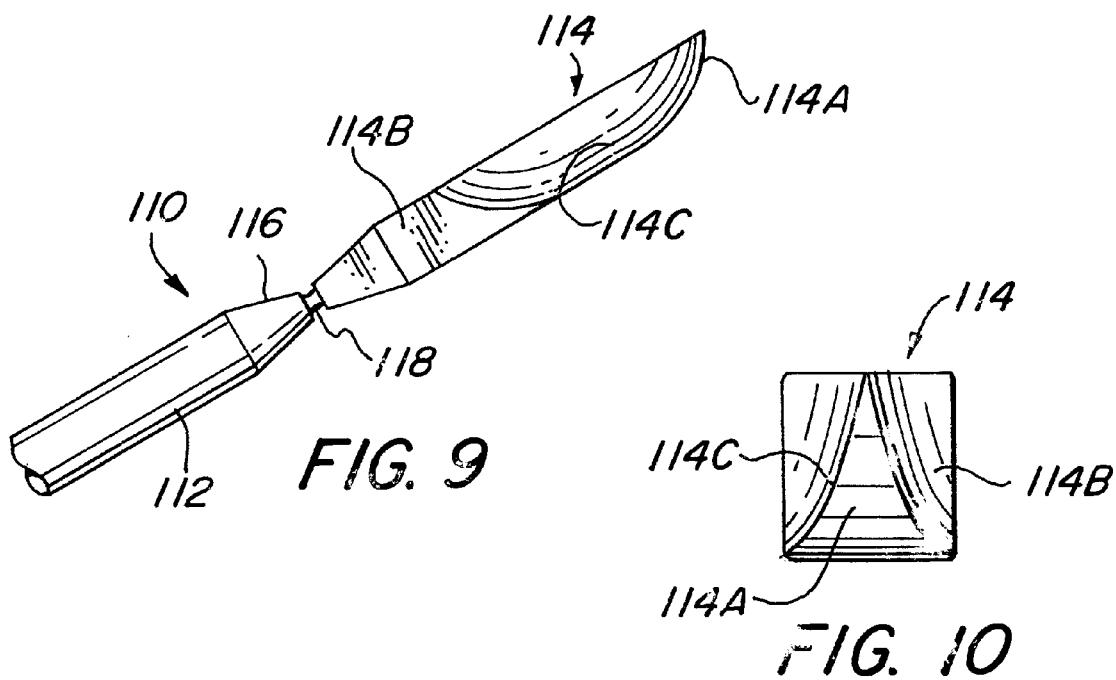
FIG. 9
FIG. 10
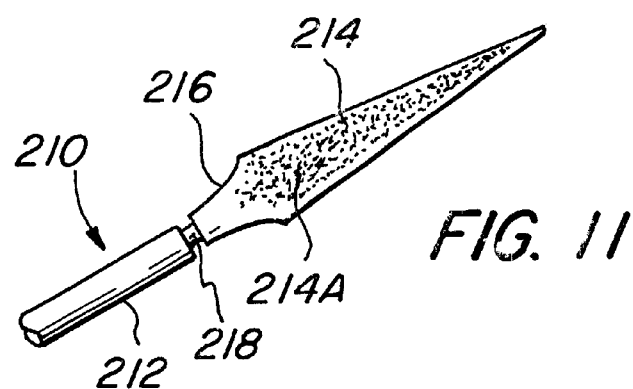
FIG. 11
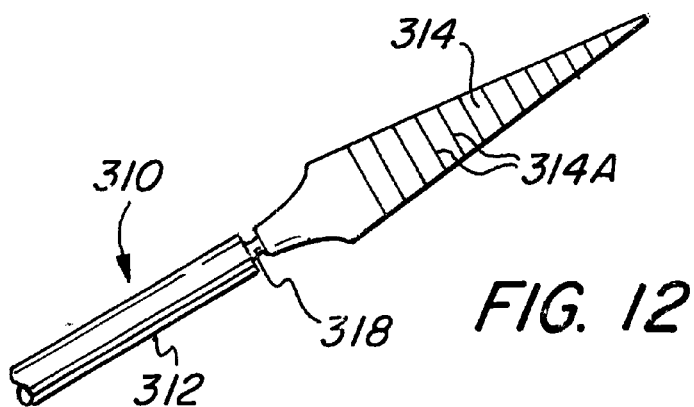
FIG. 12

DENTAL WEDGE WITH HANDLE

FIELD OF THE INVENTION

The present invention relates in general to a dental wedge, and in particular to a dental wedge having a handle permitting easy placement between teeth.

BACKGROUND OF THE INVENTION

In many dental procedures, and in particular a restorative dental procedure, dental wedges are often needed. When decay is located between two teeth, tooth material must often be removed between the two teeth. After the removal of the dental material in preparation for restoration, a matrix band is often placed between the two teeth to form a wall so as to contain the restorative dental material. However, many matrix bands are not adapted well to the bottom or gingival portions of the tooth being restored. In order to obtain a good fit with the tooth and adaptation of the matrix band to the gingival portion, a wedge is often forced into the area between the matrix band and an adjacent tooth. The purpose of the wedge is to force the gingival portion of the matrix band against the tooth, preventing the restorative material from being forced beyond the cavity preparation, which could produce a permanent irritation and possible periodontal abscess. The wedge may also be used to help force the teeth apart, allowing for the thickness of the matrix band. After placement of the restorative material, the matrix band and wedge are removed allowing the slight separation of the teeth to come together. Typically, wedges are relatively small pieces of material made of wood or plastic. They are often made in many different shapes. They are usually difficult to handle and must be picked up with forceps or other small tweezer-like appliance and forced between an adjacent tooth and the matrix band. These small wedges are difficult to hold and manipulate using conventional instruments found in the dental office. The use of a much larger dental instrument often obfuscates the view, and makes placement of the dental wedge difficult. Therefore, there is a need for a dental wedge that is more easily placed and positioned between teeth for use in dentistry.

SUMMARY OF THE INVENTION

The present invention is a dental wedge having a bendable frangible handle attached thereto. A dental wedge having a predetermined shape and cross section is attached to one end of a handle. A neck and frangible portion is positioned between the dental wedge and the handle. The handle is sufficiently attached to the dental wedge portion so as to permit convenient placement, yet can readily be detached from the dental wedge portion. In one embodiment, a bendable portion is included on the handle so as to permit angling the dental wedge for better placement. In other embodiments, different dental wedges are used.

Accordingly, it is an object of the present invention to provide easy placement of a dental wedge.

It is a further object of the present invention to reduce or eliminate the possibility of cross-contamination in the use of a dental wedge.

It is an advantage of the present invention that it is inexpensive to manufacture and is disposable after a single use.

It is a further advantage of the present invention that the dental wedge portion may be placed or positioned between teeth without the use of any other device such as forceps, pliers or tweezers.

It is a feature of the present invention that a handle portion is attached to the wedge portion.

It is a further feature of the present invention that the handle is frangibly attached to the wedge portion.

It is yet another feature of the present invention that a portion of the handle is bendable to permit easy placement of the wedge.

These and other objects, advantages, and features will become readily apparent in view of the following more detailed description.

BRIEF DESCRIPTION OF THE DRAWINGS

FIG. 1 illustrates an embodiment of the present invention.

FIG. 2 illustrates a portion of the embodiment illustrated in FIG. 1 slightly rotated.

FIG. 3 schematically illustrates different points along the dental wedge portion of the present invention.

FIG. 4 is a cross-section taken along line 4—4 in FIG. 3.

FIG. 5 is a cross-section taken along line 5—5 in FIG. 3.

FIG. 6 schematically illustrates the placement of the present invention between teeth in preparing for a dental restoration.

FIG. 7 schematically illustrates the dental wedge portion of the present invention after removal of the handle portion.

FIG. 8 is a side elevational view illustrating placement of the dental wedge portion of the present invention.

FIG. 9 is a side elevational view illustrating a portion of another embodiment of the present invention having a different shape dental wedge portion.

FIG. 10 is a front elevational view of the dental wedge portion of the present invention illustrated in FIG. 9.

FIG. 11 is a side elevational view illustrating a portion of another embodiment of the present invention having a different dental wedge portion.

FIG. 12 is a side elevational view illustrating a portion of another embodiment of the present invention having another different dental wedge portion.

DETAILED DESCRIPTION OF THE PREFERRED EMBODIMENT

Figure 13:
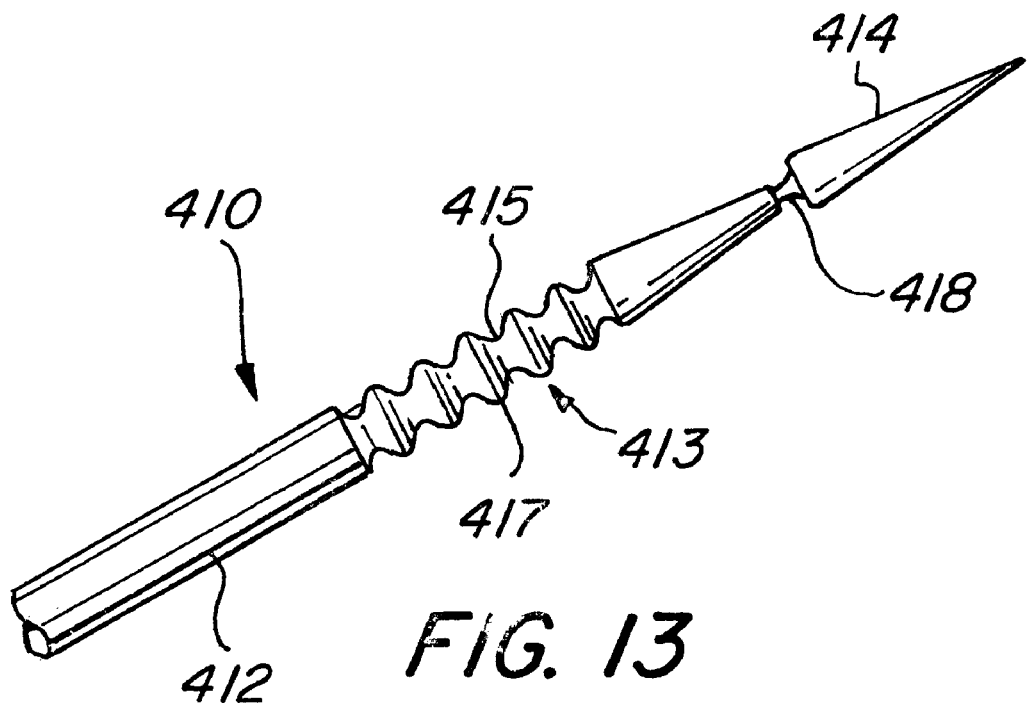
FIG. 13 is a side elevational view of a portion of the present invention illustrating a bendable portion.

FIG. 1 illustrates an embodiment of the present invention, a dental wedge with a frangible handle 10. A handle 12 is attached to a dental wedge 14. The dental wedge 14 may be of any desired shape suitable for wedging. A neck 16 having a reduced lateral dimension or diameter is placed between the dental wedge 14 and the handle portion 12. A frangible portion 18 has a further reduced diameter or lateral dimension. The dental wedge and handle 10 may be made of any suitable material, for example, plastic or wood. Preferably, the dental wedge with handle 10 is made of a suitable plastic. The frangible portion 18 permits the dental wedge portion 14 and the handle portion 12 to be separated. The handle 12 is preferably substantially longer than the wedge 14. The handle 12 may be as much as four times longer than the length of the dental wedge 14. For example, if the dental wedge 14 is approximately 0.5 inches or 1.3 centimeters long or longer, the handle may be approximately 4 inches or 6.2 centimeters long or longer. The substantial length of the handle 12 permits easy grasping and placement of the dental wedge 14.

FIG. 2 illustrates a portion of the present invention rotated slightly from that of FIG. 1 along the longitudinal axis. A flat face of the dental wedge portion 14 is more clearly illustrated in FIG. 2.

FIG. 3 illustrates different points along the longitudinal length of the dental wedge portion 14. At a location 14A, the lateral dimension of the dental wedge 14 is greater than that at location 14B.

FIG. 4 illustrates the cross-section taken along line 4—4 illustrated in FIG. 3 at location 14A. The cross-section is generally triangular and may be an equilateral triangle or an isosceles triangle. However, other shapes or triangular cross-sections may also be used.

FIG. 5 illustrates the cross-section taken along line 5—5 at point 14B in FIG. 3. The cross-section at location 14B is also substantially a triangle. However, the lateral dimension at location 14B is less than that at location 14A illustrated in FIG. 3. Accordingly, when the apex or point of the dental wedge portion 14 is inserted between teeth, it acts as a wedge to separate or apply pressure to the teeth or other abutting surface.

FIG. 6 illustrates the operation of the present invention and its application in a restorative dental procedure. Two teeth 20 and 21 adjacent to each other form a gap between which the dental wedge portion 14 is inserted. Tooth 21, having a prepared cavity 24 therein and which is to be filled with a dental restorative material, has a matrix band 22 placed adjacent thereto. The matrix band 22 forms a wall so as to contain the dental restorative material. The matrix band may generally encircle the whole tooth 21, but for illustrative purposes only a portion thereof is shown. The dental wedge portion 14 is inserted with handle portion 12 in the direction of arrow 26 between the two teeth 20 and 21. One side or face of the dental wedge 14 abuts tooth 20, with the other side or face of the dental wedge 14 abutting the matrix band 22. This causes the matrix band 22 to be firmly positioned adjacent the base of tooth 21. Subsequent to positioning the dental wedge portion 14, the handle 12 may remain in place or, if desired to provide additional working area, be removed by either rocking or moving the handle portion 12 back and forth in the direction of arrow 28. The handle portion 12 may also be rotated in the direction of arrow 30. Either method of rocking, rotating, spinning, twisting or combination will result in the frangible portion 18 breaking. This results in the handle portion 12 and the wedge portion 14 to become separate.

FIG. 7 illustrates the dental wedge portion 14 remaining between the teeth 20 and 21 after the handle portion has been separated from the dental wedge portion 14. Prepared cavity 24 may then be filled with a dental restorative. With the handle portion removed, additional working area is obtained.

FIG. 8 is a side elevational view illustrating the positioning of the dental wedge portion 14 at the base of the tooth 21. This holds the matrix band 22 in tight conformance to the base of the tooth 21, permitting a dental restorative to be filled within the prepared cavity 24.

FIG. 9 illustrates another embodiment of the present invention. In this embodiment, the dental wedge and handle 110 has a handle portion 112 and a dental wedge portion 114. Separating the dental wedge portion 114 and the handle portion 112 is a neck portion 116. A frangible portion 118 is formed within the neck portion 116. The frangible portion 118 may have a reduced lateral dimension than that of neck portion 116. Alternatively, neck portion 116 may be sufficiently frangible so that any further reduced frangible portion 118 may not be needed. The dental wedge portion 114 has a curved front 114A and a rectilinear rear portion 114B. The face 114C or angled sides function as the wedge. This shape provides a more anatomical wedge.

FIG. 10 is a front elevational view illustrating the dental wedge 114. The curved front 114A and the rectilinear rear portion 114B are more clearly illustrated.

FIG. 11 illustrates another embodiment of the present invention of a dental wedge and handle 210. In this embodiment, handle portion 212 is attached to the dental wedge portion 214 by a frangible portion 218. A neck portion 216 provides a transition between the dental wedge portion 214 and the frangible portion 218. The dental wedge portion 214 may have a triangular cross-section having three sides or faces. Each side or face may have a textured surface 214A so as to facilitate gripping between the teeth or matrix band. The textured surface 214A may be a roughened surface, dimples, or other gripping surface.

FIG. 12 illustrates another embodiment of the present invention, a dental wedge and frangible handle 310. A handle portion 312 is placed adjacent the dental wedge portion 314 and is separated by a frangible portion 318. The dental wedge portion 314 may have a generally triangular cross-section having three sides or faces with ribs 314A placed laterally across each of the sides or faces. The ribs 314A may be raised or recessed portions placed on the face of the dental wedge portion 314.

Figure 14:
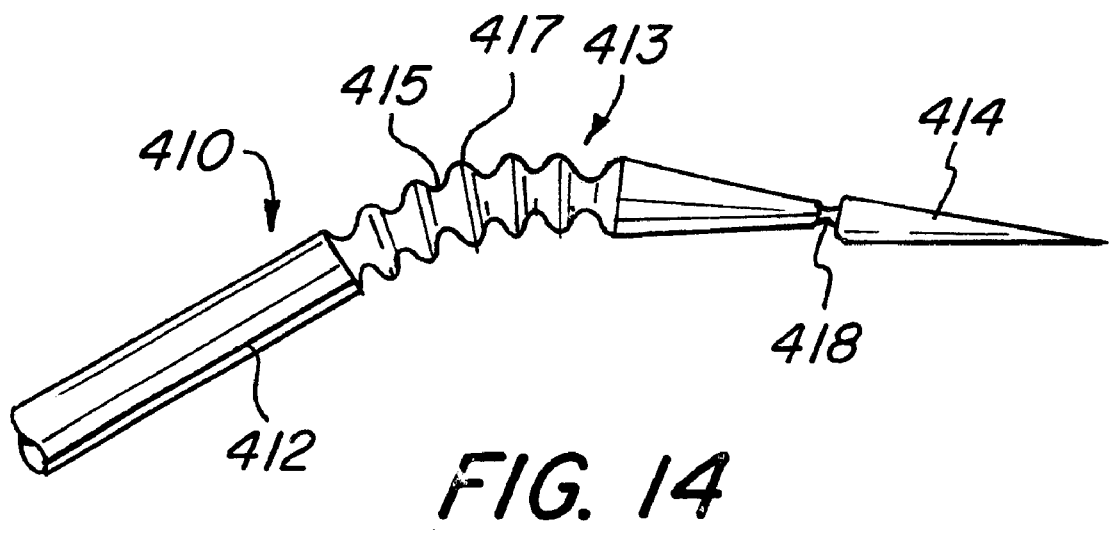
FIG. 14 is a side elevational view illustrating bending of the embodiment illustrated in FIG. 13.

FIGS. 13 and 14 illustrates yet another embodiment of the present invention of a dental wedge and frangible handle 410. However, in this embodiment a means for bending or a bendable portion 413 is utilized. The dental wedge with a frangible handle 410 has a handle portion 412 and a dental wedge portion 414. Adjacent the dental wedge portion 414 is a frangible portion 418. Adjacent the frangible portion 418 is a bendable portion 413. The bendable portion 413 may take a variety of forms as long as it results in a bendable portion. However, in this embodiment, the bendable portion comprises a plurality of valleys 415 and peaks 417. Therefore, alternating reduced lateral dimensions and increased lateral dimensions exist along the bendable portion 413. Accordingly, the dental wedge and frangible handle 410 can be bent along the bendable portion 413 so as to facilitate placement of a dental wedge portion 414. The bendable portion may take other forms, for example a crimp. The bendable portion 413 may also take other equivalent forms. FIG. 14 illustrates the dental wedge and frangible handle 410 being bent along the bendable portion 413. The bendable portion 413 greatly facilitates the positioning of the dental wedge portion 414 between teeth in hard to reach areas such as in the back of the mouth.

Accordingly, the present invention has many advantages over the dental wedges of the prior art. The possibility of losing a relatively small wedge in a patient's mouth prior to placement is reduced. Additionally, secure placement of the wedge can be assured prior to removal of the handle. However, should the handle be desired to be retained, it will also facilitate removal or readjustment of the dental wedge. A dentist or dental technician can easily position the wedge with must less dexterity than required in conventional dental wedge placement using forceps, tweezers, or pliers. Additionally, the need for sterilizing instruments use to place prior wedges is eliminated. As a result, the possibility of cross-contamination is eliminated or substantially reduced. The bendable portion of the handle in one embodiment allows the operator to bend the dental wedge and frangible handle as necessary for convenient placement of the wedge portion. After the desired wedge position is obtained, pressure is applied, inserting the wedge between the teeth. When the applied pressure produces no further wedge insertion, the pressure is removed. The handle may then be rotated, spun, twisted, or bent to separate the wedge portion from the handle portion. The handle can then be discarded. Should any additional wedging pressure be needed, a new dental wedge and frangible handle may be used or the wedge portion may be readjusted using conventional means. After completion of the dental procedure, the dental wedge can be easily removed. The present invention therefore greatly facilitates the placement of dental wedges in various dental procedures.

Accordingly, although the preferred embodiments have been illustrated and described, it will be obvious to those skilled in the art that various modifications may be made without departing from the spirit and scope of this invention.

What is claimed is:

1. A dental wedging instrument comprising:

a dental wedge portion;

a handle portion having a first lateral dimension;

a frangible portion positioned between said dental wedge portion and said handle portion, said frangible portion having a second lateral dimension, the second lateral dimension being less than the first lateral dimension, and a bendable portion placed adjacent said handle portion.

2. A dental wedging instrument as in claim 1 wherein:

said dental wedge portion and said handle portion are made of plastic.

3. A dental wedging instrument as in claim 1 wherein:

said bendable portion comprises a plurality of peaks and valleys.

4. A dental wedging instrument as in claim 1, wherein:

said dental wedge portion has a plurality of surfaces and further comprises a plurality of ribs formed on the plurality of surfaces.

5. A dental wedging instrument comprising:

a dental wedge portion;

a handle portion substantially longer than said dental wedge portion, said handle portion frangibly attached to said dental wedge portion so that said dental wedge portion has a distal end unobstructed by said handle portion; and a neck portion positioned between said dental wedge portion and said handle portion.

6. A dental wedging instrument comprising:

a dental wedge portion;

a handle portion having a first diameter;

a neck portion positioned between said dental wedge portion and said handle portion, said neck portion having a second diameter, the second diameter being less than the first diameter of said handle portion;

a frangible portion positioned between said dental wedge portion and said handle portion, said frangible portion having a third diameter, the third diameter being less than the second diameter of said neck portion; and a bendable portion positioned adjacent said neck portion, whereby said dental wedge portion is easily positioned between teeth and said handle portion may be separated from said dental wedge portion.

7. A dental instrument comprising:

a dental wedge portion having a first length; and an elongated handle portion having two ends and a second length frangibly attached to said dental wedge portion at one end of the two ends of the elongated handle portion, the second length being substantially greater than the first length, whereby said elongated handle portion permits easy grasping and placement of said dental wedge.

8. A dental instrument as in claim 7 wherein:

the second length is at least four times greater than the first length.

9. A dental instrument as in claim 7 wherein:

the first length is greater than 0.5 inches or 1.3 centimeters and the second length is greater than 4.0 inches or 6.2 centimeters.

10. A method of wedging teeth comprising the steps of:

placing a wedge with a handle attached between two adjacent teeth;

rotating the handle until the handle separates from the wedge;

filling a prepared cavity with a dental restorative; and removing the wedge from between the two adjacent teeth, whereby the wedge is easily inserted between the two adjacent teeth.

11. A removable dental wedge for temporary placement between teeth during a dental procedure comprising:

an elongated rod handle having two ends;

a dental wedge formed on one end of said elongated rod handle, a neck between said elongated rod handle and said dental wedge; and a frangible portion placed on said neck, whereby said dental wedge is capable of being easily positioned between teeth by hand and separated from said elongated rod handle and subsequently removed after the dental procedure.

12. A removable dental wedge as in claim 11 wherein:

said elongated rod handle and said dental wedge are made of plastic.

* * * * *